United States Patent [19]

Stanko

[11] Patent Number: 5,294,641
[45] Date of Patent: Mar. 15, 1994

[54] METHOD FOR TREATING A MEDICAL PATIENT FOR CARDIAC TRAUMA

[75] Inventor: Ronald T. Stanko, Pittsburgh, Pa.

[73] Assignee: Montefiore - University Hospital, Pittsburgh, Pa.

[21] Appl. No.: 802,062

[22] Filed: Nov. 27, 1991

[51] Int. Cl.$^5$ ............... A61K 31/24; A61K 31/19
[52] U.S. Cl. ........................... 514/540; 514/574
[58] Field of Search ................. 514/557, 574, 540

[56] References Cited

U.S. PATENT DOCUMENTS 4,988,515  1/1991  Buckberg ....................... 514/561
5,147,650  9/1992  Fregly et al. ................... 514/557

FOREIGN PATENT DOCUMENTS 108820  5/1984  European Pat. Off. .

OTHER PUBLICATIONS

Bünger, Rolf et al., Eur. J. Biochem. 180, 221-233 (1989).

*Primary Examiner*—Frederick E. Waddell
*Assistant Examiner*—Raymond J. Henley, III
*Attorney, Agent, or Firm*—Harry B. Keck

[57] ABSTRACT

A method for treating a medical patient prior to or during heart trauma, e.g., myocardial infarction, angina and ischemia. An effective dosage of pyruvate is introduced into the patient to increase the patient's cardiac output and stroke volume, to decrease the patient's heart rate and to reduce the oxygen demand of the patient's heart. The dosage may be introduced intravenously into the patient or orally as a component of the patient's diet. The oral feeding method is especially useful for surgical patients prior to surgical procedures which are likely to encourage cardiac trauma and useful for patients exhibiting symptoms of chronic congestive heart failure.

9 Claims, No Drawings

METHOD FOR TREATING A MEDICAL PATIENT FOR CARDIAC TRAUMA

BACKGROUND OF THE INVENTION

1. Field of the Invention

The present invention provides a method (a) for treating a medical patient to prepare the patient for surgical procedures involving the heart, lungs, veins, arteries or other vital organs, which procedures are accompanied by cardiac trauma, i.e., ischemia, and (b) for treating a medical patient experiencing cardiac trauma. The invention provides for introducing an effective dosage of pyruvate into the patient's bloodstream prior to and/or during the cardiac trauma.

2. Description of the Prior Art

Pyruvate and mixtures of pyruvate with dihydroxyacetone have been described for a number of beneficial results:

U.S. Pat. No. 4,158,057 describes oral administration of pyruvate and dihydroxyacetone to prevent excessive accumulation of fatty deposits in a mammal liver due to ethanol ingestion.

U.S. Pat. No. 4,351,835 describes oral administration of pyruvate and dihydroxyacetone to reduce an expected weight gain from a given diet or to induce a weight loss in a mammal. The patent also describes oral administration of pyruvate and dihydroxyacetone to athletes prior to strenuous athletic events to increase endurance and/or performance.

U.S. Pat. No. 4,415,575 describes oral administration of pyruvate and dihydroxyacetone to increase the body protein concentration in a mammal.

U.S. Pat. No. 4,458,937 describes oral administration of pyruvate to a mammal to induce a weight loss or reduce an expected weight gain from a given diet.

U.S. Pat. No. 4,645,764 describes oral administration to a living being of pyruvate and dihydroxyacetone to induce a weight loss or to reduce an expected weight gain from a given diet and for inhibiting body fat while increasing body protein concentration.

U.S. Pat. No. 4,812,478 describes oral administration of dihydroxyacetone to an animal to induce a weight loss or to reduce an expected weight gain from a given diet.

These described results of oral administration of pyruvate and pyruvate with dihydroxyacetone are of great interest for medical patients who ingest ethanol; medical patients having fatty liver deposits or tendencies toward fatty liver deposits; medical patients who are obese or have a tendency toward obesity; normal subjects desiring to lose body weight or to retard body weight increase; normal patients, particularly athletes, who desire to increase endurance; and medical patients having diabetic tendencies.

U.S. Pat. No. 4,874,790 describes the use of pyruvate as a treatment for patients having diabetic tendencies.

The use of pyruvate to treat ischemia and to increase inotropism in hearts has been described:

K. E. SOMMERS et al, PYRUVATE IMPROVES POSTISCHEMIC MIOCARDIAL FUNCTION AND ATP RECOVERY: A 31P NMR SPECTROSCOPY STUDY, SURGICAL FORUM VOL XLI, 1990, pages 241-3;

R. M. MENTZER, JR. et al, EFFECT OF PYRUVATE ON REGIONAL VENTRICULAR FUNCTION IN NORMAL AND STUNNED MYOCARDIUM, ANN. SURG. May 1989, pages 629-634;

ROLF BUNGER et al, PYRUVATE-ENHANCED PHOSPHORYLATION POTENTIAL AND INOTROPISM IN NORMOXIC AND POSTISCHEMIC ISOLATED WORKING HEART, EUR. J. BIOCHEM, Feb. 1989, pages 221-233.

It is an object of this invention to increase the cardiac output of a human in need thereof without concurrently increasing the cardiac oxygen demand of the human.

STATEMENT OF THE PRESENT INVENTION

Surgical procedures involving the heart, lungs, veins, arteries and other vital organs are accompanied by heart trauma, especially ischemia. Ischemia is defined as a lack of oxygen in an organ; heart ischemia is defined as a lack of oxygen in the heart.

According to the present invention the adverse effects of ischemia are offset by introducing a therapeutic quantity of pyruvate into the blood stream of the patient prior to the surgical procedure to increase the patient's cardiac output, to increase the patient's heart stroke volume and, unexpectedly, to increase the patient's heart stroke volume and, unexpectedly, to reduce the oxygen demand of the patient's heart.

The treatment may be initiated several weeks prior to scheduled surgery and may be continued to and through the surgical procedure. For unscheduled surgery, the treatment may commence as soon as feasible prior to and throughout the surgical procedure. For cardiac trauma which may or may not result in surgery, the treatment may begin as soon as cardiac trauma symptoms are suspected.

The pyruvate may be in the form of organic salts, e.g., calcium or sodium salts of pyruvic acid; or esters of pyruvic acid such as ethyl amino pyruvate.

Cardiac trauma also occurs in medical patients. Many patients seek medical attention when experiencing chest pains, angina, myocardial infarction and other cardiac disorders. The standard treatment for such patients is to introduce liquid solutions intravenously into the patient's circulatory system. Such liquid solutions are available in a variety of compositions. Some liquid solutions contain vitamins and selected minerals and sugars. The liquid solutions also may contain specific pharmaceuticals as anti-coagulants, blood thinners, and the like. The patient may also receive dosages of inotropic agents such as dopamine, dobutamine or isuprel. The known inotropic agents increase the contractility of the heart and increase the heart rate, but also increase the oxygen demand of the heart. The inotropic agents may be included in the saline solutions which are available.

Adding pyruvate to such saline solutions provides a convenient system for introducing pyruvate into the cardiac trauma patient. Pyruvate, like known inotropic agents increases the contractility of the heart and increases the heart rate. However the pyruvate does not increase the oxygen demand of the heart, but unexpectedly lowers the oxygen demand of the heart.

A medical patient who is about to undergo surgical procedures which are likely to encourage cardiac trauma, e.g., ischemia, preferably is prepared for the surgical procedure by oral dosages of pyruvate for a treatment period of several days to several weeks prior to the scheduled surgery. Typical surgical procedures which are likely to develop cardiac trauma include surgery involving the heart, lungs, veins, arteries, or other vital organs. A preferred pyruvate oral dosage is from 5 to 15 percent of the patient's caloric intake throughout the treatment period.

The pyruvate dosage has been observed to increase the heart output and to increase the stroke volume of the heart and concurrently to reduce the oxygen requirement of the heart. These three benefits enable the heart to perform its normal functions more easily. These benefits to the cardiac trauma patient will improve opportunities for effective treatment in the cases of genuine cardiac malfunctions and will cause no objectionable side effects in patients having false symptoms of cardiac trauma.

Heart output (or cardiac output) has been defined as the quantity of blood pumped by the left ventricle into the aorta each minute. Heart output for young healthy adult males averages 5.6 liters per minute. The stroke volume is the quantity of blood pumped by each beat of the left ventricle. The heart rate is the number of heart beats per minute. The product of heart rate (beats/minute) and stroke volume (volume/beat) yields the cardiac output (volume/minute).

PREFERRED EMBODIMENTS

In a preferred procedure, a medical patient experiencing cardiac trauma receives a liquid drip solution immediately containing from about 2-20 grams pyruvate per liter of solution. The pyruvate may be in the form of metal salts of pyruvic acid or may be in the form organic esters of pyruvic acid, for example, ethyl amino pyruvate. The saline drip is continued until the patient is normalized. If immediate surgery is indicated, the liquid drip will continue throughout the surgery and thereafter until the patient is normalized.

An alternative procedure, when time is available, is to provide oral dosages of pyruvate for days or weeks prior to an anticipated cardiac trauma, e.g., prior to scheduled surgery. Immediately prior to and during surgery, the saline drip should be employed.

As a further alternative, patients having chronic congestive heart failure symptoms may take effective oral dosages of pyruvate to decrease heart rate, to increase stroke volume and to reduce the oxygen demand of the heart. Liquid pyruvate in drinks is preferred. Pyruvate in a confection is a convenient alternative, e.g., cookies, candies. Pyruvate may be substituted in whole or in part for digitalis in treating chronic congestive heart failure patents.

EXAMPLE I

A control group of 20 human patients was fed a mixture of sodium and calcium pyruvate continuingly over a period of 6 weeks. The patients received 26-44 grams of pyruvate daily corresponding to about 7% of the total caloric intake of each patient over the six-week period.

At the end of the six-week period, the heart rate for the patients (beats/minute) decreased 9%. The diastolic blood pressure decreased 6%. The rate pressure product (rpp), measured as the product of systolic blood pressure and heart rate, decreased 13%.

The rate pressure product (rpp) is known to be an indirect measure of the oxygen requirement of the heart. Hence the oxygen demand of the patients was decreased.

EXAMPLE II

In another experiment, eight human subjects were fed sodium and calcium pyruvate for a period of one week continuingly at the rate of 15% of the total calories of each patient. The total pyruvate did not exceed 400 calories daily for any one patient per day.

Prior to and following the treatment period, the subjects carried out arm exercise for 90 minutes or leg exercise for 60 minutes. At the end of the exercise, the cardiac output of each subject was measured. The cardiac output (liters/minute) increased by 2.3%. The cardiac stroke volume (ml/min) increased by 5%.

The cardiac output and stroke volume of each subject was measured before and after the one week period. The increases are reported in TABLE I:

TABLE I

| SUBJECT | CARDIAC OUTPUT INCREASE % | STROKE VOLUME INCREASE % |
|---|---|---|
| 1 | 2.0 | 4.5 |
| 2 | 1.7 | 4.3 |
| 3 | 1.0 | 4.8 |
| 4 | 1.0 | 2.9 |
| 5 | 0 | 1.0 |
| 6 | 6.8 | 10.9 |
| 7 | 5.2 | 10.7 |
| 8 | 1.0 | 1.0 |
| $\bar{X}$ (average) | 2.3 ± 0.8 | 5.0 ± 1.4 |
| Deviation | $p < 0.05$ | $p < 0.05$ |

The deviation ($p<0.05$) indicates that the reported values are statistically significant.

By increasing the cardiac output and stroke volume and reducing the cardiac oxygen demand, the patient's heart experiences increased effectiveness without increase in effort (which equates to exercise).

Oral ingestion of pyruvate preferably is in the form of a liquid food containing the pyruvate. Liquid diet preparations are especially useful. The pyruvate may be included in solid foods, such as confections, e.g., cookies, cakes, candies.

EXAMPLE III

Six laboratory dogs, weight about 17 Kg each, were individually anaesthetized. Blood tubes were inserted into the (a) aorta; (b) vena cava; and (c) femoral artery of each dog. A pressure sensor was placed in the left ventricle of each dog. An EKG was installed for each dog to record the EKG waves.

A pyruvate infusion was introduced into the superior vena cava of each dog. The concentration of pyruvate started at 0.25 mg/minute/kg of dog weight and increased as shown in TABLE II.

TABLE II

| Time (Minutes) | INFUSION CONCENTRATION | |
|---|---|---|
| 0-15 | 0.25 | mg/minute/Kg dog weight |
| 15-30 | 0.5 | |
| 30-45 | 1.0 | |
| 45-60 | 2.0 | |
| 60-75 | 4.0 | |
| 75-90 | 8.0 | |
| 90-105 | 16.0 | |

Note that the test continued for 105 minutes with the pyruvate concentration doubled every 15 minutes.

Throughout the test:
(a) Sensors measured blood flow (volume/time).
(b) The heart rate (beats/minute) were measured.
(c) Diastolic blood pressure (gms/area).

(d) Blood samples were taken from an artery and from a vein. Oxygen analyses of the two samples established the oxygen demand.

In all cases the oxygen demand decreased throughout the text.

Relevant observations are set forth in TABLE III.

TABLE III

PYRUVATE TESTS WITH ANAESTHETIZED DOGS
All individual tests were averaged and normalized.

| Time (Minutes) | Pyruvate Concentration (a) | $\Delta p/\Delta t$ (b) | Content $O_2$ | Content $CO_2$ | Cardiac Output | Heart Rate |
|---|---|---|---|---|---|---|
| 0 | 0 | 1.00 (c) | 1.00 (c) | 1.00 (c) | 1.00 (c) | 1.00 (c) |
| 18 | 0.25 | 0.99 | 0.95 | 0.95 | 0.92 | 0.99 |
| 33 | 0.50 | 0.98 | 0.99 | 0.93 | 0.98 | 0.98 |
| 49 | 1.00 | 0.96 | 0.90 | 0.84 | 0.93 | 0.95 |
| 64 | 2.00 | 0.86 | 0.90 | 0.93 | 0.92 | 0.88 |
| 80 | 4.00 | 1.02 | 0.98 | 0.84 | 1.01 | 0.86 |
| 96 | 8.00 | 1.14 | 0.98 | 0.87 | 1.03 | 0.82 |
| 107 | 16.00 | 1.45 (d) | 1.05 (e) | 0.94 (e) | 1.17 | 0.83 |

(a) - Mg pyruvate/minute/Kg dog weight.
(b) - Change in blood pressure with time indicates the contractility of the heart.
(c) - Arbitrary "normal" value.
(d) - The contractility increased 45% after the pyruvate became effective.
(e) - The difference between oxygen content and $CO_2$ content indicates the oxygen utilization. There was a 10% decrease (1.05-0.94).

The dog tests of EXAMPLE III indicate that cardiac output increases, heart rate decreases and oxygen demand decreases when sufficient pyruvate is in the animal's blood system.

Note that the initial effects of pyruvate at low concentrations did not predict the favorable effects of pyruvate after a suitable concentration was delivered.

I claim:

1. A method for increasing the cardiac output of a human, in need thereof without concurrently increasing the cardiac oxygen demand of said human which comprises feeding said human, orally or intravenously, an effective dosage of pyruvate.

2. A method of increasing the cardiac output of a patient in preparation for a surgery likely to result in cardiac trauma without concurrently increasing said patient's cardiac oxygen demand which comprises feeding said patient orally an effective dosage of pyruvate continuously over a preparation period prior to said surgery.

3. The method of claim 2 wherein the pyruvate dosage provides 5-15 weight percent of the patient's total caloric intake over said preparation period.

4. The method of claim 1 wherein the pyruvate is included in a liquid drip solution containing 2 to 20 weight percent pyruvate.

5. The method of claim 3 wherein the pyruvate is included in a confection.

6. The method of claim 1 wherein the pyruvate is a metal salt of pyruvic acid.

7. The method of claim 1 wherein the pyruvate is an organic ester of pyruvic acid.

8. The method of claim 7 wherein the pyruvate is ethyl amino pyruvate.

9. A method for increasing the cardiac output of a medical patient experiencing surgery involving the heart or other vital organ without concurrently increasing said patient's cardiac oxygen demand which comprises introducing an effective cardiac output increasing amount of pyruvate into said patient by an intravenous liquid drip solution containing pyruvate throughout said surgery.

* * * * *